(12) United States Patent
Saito et al.

(10) Patent No.: US 6,492,545 B2
(45) Date of Patent: Dec. 10, 2002

(54) PROCESS FOR PRODUCING OPTICALLY ACTIVE ALCOHOL

(75) Inventors: Takao Saito, Kanagawa (JP); Tohru Yokozawa, Kanagawa (JP); Kazuhiko Matsumura, Kanagawa (JP); Noboru Sayo, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/909,803

(22) Filed: Jul. 23, 2001

(65) Prior Publication Data

US 2002/0035283 A1 Mar. 21, 2002

(30) Foreign Application Priority Data

Jul. 25, 2000 (JP) ........................................ 2000-223521

(51) Int. Cl.⁷ ........................ C07C 69/66; C07C 69/76; C07C 69/74
(52) U.S. Cl. ........................ 560/179; 560/60; 560/126; 560/184; 558/252; 564/201
(58) Field of Search .......................... 560/179, 60, 126, 560/184; 558/252; 564/201

(56) References Cited

U.S. PATENT DOCUMENTS 4,933,482 A * 6/1990 Sayo et al.
5,872,273 A * 2/1999 Saito et al.

FOREIGN PATENT DOCUMENTS

| EP | 0 295 109 A1 | 12/1988 |
| EP | 0 850 945 A1 | 7/1998 |
| EP | 0 955 303 A2 | 11/1999 |

OTHER PUBLICATIONS

European Search Report dated Nov. 30, 2001.

* cited by examiner

Primary Examiner—Alan L. Rotman
Assistant Examiner—Héctor M Reyes
(74) Attorney, Agent, or Firm—Sughrue Mion, PLLC

(57) ABSTRACT

A novel process in which an optically active alcohol compound having a desired absolute configuration and a high optical purity can be obtained by asymmetrically hydrogenating a β-keto acid compound through a simple operation. An optically active alcohol represented by general formula (III) as defined is obtained by asymmetrically hydrogenating a β-keto ester compound represented by general formula (I) as defined in the presence of at least one ruthenium complex having as a ligand an optically active tertiary diphosphine compound represented by general formula (II) as defined.

3 Claims, No Drawings

PROCESS FOR PRODUCING OPTICALLY ACTIVE ALCOHOL

FIELD OF THE INVENTION

The present invention relates to a novel process for producing an optically active alcohol. More particularly, the invention relates to a novel process suitable for the practical production of an optically active β-hydroxy acid compound useful as an intermediate for medicines or as a functional material, etc.

BACKGROUND ART

Conventionally known methods for synthesizing an optically active alcohol compound include 1) a method in which an enzyme such as a baker's yeast is used and 2) a method in which a metal complex is used to asymmetrically hydrogenate a carbonyl compound. In particular, with respect to the latter method for asymmetric hydrogenation, many proposals have been made. Known examples thereof include: (1) a method in which a carbonyl compound having a functional group is asymmetrically hydrogenated in the presence of an optically active ruthenium complex catalyst (R. Noyori, *Asymmetric Catalysis in Organic Synthesis*, pp.56–82 (1994)); (2) a method in which a 1,3-dicarbonyl compound is asymmetrically hydrogenated with the aid of a ruthenium-diphosphine complex (*Tetrahedron Asymmetry*, Vol.8, pp.3327–3355 (1997)); (3) a method of asymmetric hydrogenation using a ruthenium-optically active phosphine complex (JP-B-6-99367) (the term "JP-B" as used herein means an "examined Japanese patent publication"); (4) a method in which the hydrogen transfer reduction reaction of a carbonyl compound is utilized in the presence of an asymmetric complex catalyst comprising ruthenium, rhodium, or iridium (*Chem. Rev.*, Vol.92, pp.1051–1069 (1992)); (5) a method in which a carbonyl compound is asymmetrically hydrogenated with the aid of a nickel complex modified with tartaric acid (*Yu Kagaku*, pp.828–831 (1980), and Y. Izumi, *Advances in Catalysis*, Vol.32, p.215 (1983)); (6) a method in which the asymmetric hydrosilylation reaction of a carbonyl compound is utilized (J. D. Morrison, *Asymmetric Synthesis*, Vol.5, Chap.4 (1985), and *J. Organomet. Chem.*, Vol.346, pp.413–424 (1988)); (7) a method in which a carbonyl compound is reduced with a borane in the presence of an asymmetric ligand (*J. Chem. Soc., Perkin Trans. I*, pp.2039–2044 (1985), and *J. Am. Chem. Soc.*, Vol.109, pp.5551–5553 (1987)); and (8) a method in which an acetophenone compound is asymmetrically hydrogenated in the presence of potassium hydroxide, an optically active diamine, and an asymmetric ruthenium complex catalyst (*J. Am. Chem. Soc.*, Vol.117, pp.2675–2676 (1995)).

However, the above-described conventional methods for synthesizing an optically active alcohol have the following drawbacks. The synthesis method using an enzyme requires a complicated procedure and is restricted in substrates usable in the reaction. In addition, the alcohol compounds which can be obtained by the method are limited to those having a specific absolute configuration. On the other hand, the synthesis methods using a transition metal catalyst for asymmetric hydrogenation have problems that the rate of reaction is low and the optical purity of the optically active alcohol compound obtained by the asymmetric hydrogenation of a β-keto ester compound is insufficient, although various transition metal complex catalysts have been reported.

Especially in the fields of medicines and functional materials, it is important to obtain an optically active alcohol compound having a specific absolute configuration and a high optical purity and it has hence been necessary to overcome the above-described problems of the conventional methods.

Accordingly, an object of the invention is to provide a novel process in which an optically active alcohol compound having a desired absolute configuration and a high optical purity can be obtained through the asymmetric hydrogenation of a β-keto ester compound.

SUMMARY OF THE INVENTION

Under these circumstances, the present inventors made intensive investigations. As a result, it has been found that when a β-keto ester compound is asymmetrically hydrogenated with the aid of a ruthenium metal complex having as a ligand an optically active [4,4'-bis-1,3-benzodioxol]-5,5'-diylbis(diphenylphosphine) (hereinafter also referred to as "SEGPHOS" simply), then the corresponding optically active alcohol having a high optical purity is obtained. As a result of further extensive studies by the present inventors, the invention has finally been completed.

The invention provides a process for producing an optically active alcohol represented by the following general formula (III):

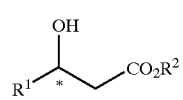

(III)

(wherein $R^1$ represents a $C_1$–$C_{15}$ alkyl group which may have one or more substituents (selected from halogen atoms, a hydroxyl group, an amino group, amino groups protected by a protective group, amino groups substituted with one or more $C_1$–$C_4$ lower alkyl groups, amino groups protected by a mineral acid or organic acid, a benzyloxy group, $C_1$–$C_4$ lower alkoxy groups, $C_1$–$C_4$ lower alkoxycarbonyl groups, and aryl groups) or an aryl group; and $R^2$ represents a $C_1$–$C_8$ lower alkyl group, or a benzyl group which may have one or more substituents)

which comprises asymmetrically hydrogenating a β-keto ester compound represented by the following general formula (I):

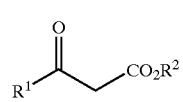

(I)

(wherein $R^1$ and $R^2$ are the same as defined above) in the presence of at least one ruthenium complex having as a ligand an optically active tertiary diphosphine compound represented by the following general formula (II):

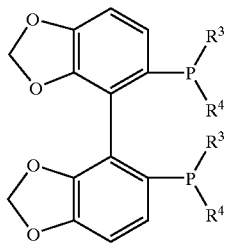

(II)

(wherein $R^3$ and $R^4$ each independently represent a cycloalkyl group, an unsubstituted or substituted phenyl group, or a five-membered heteroaromatic ring residue).

The invention further provides a process for producing the optically active alcohol which comprises conducting the asymmetric hydrogenation reaction in the presence of a specific ruthenium complex.

The invention furthermore provides a process for producing the optically active alcohol which comprises conducting the asymmetric hydrogenation reaction in the presence of a specific acid.

DETAILED DESCRIPTION OF THE INVENTION

The invention will be explained below in detail.

Preferred examples of $R^1$ in the β-keto ester compound (I) for use as a starting material in producing the optically active alcohol by the process of the invention include $C_1$–$C_{15}$ alkyl groups such as methyl, ethyl, propyl, butyl, pentyl, hexyl, octyl, decyl, undecyl, dodecyl, and tridecyl; $C_1$–$C_{15}$ alkyl groups having one or more substituents (examples of the substituents include halogen atoms, hydroxyl, amino, amino groups protected by a protective group (e.g., acetyl, benzyloxycarbonyl, or t-butoxycarbonyl), amino groups protected by a mineral acid (e.g., hydrochloric acid, sulfuric acid, bromic acid, phosphoric acid, or hydriodic acid) or by an organic acid (e.g., p-toluenesulfonic acid, methanesulfonic acid, or acetic acid), amino groups substituted with one or more $C_1$–$C_4$ lower alkyl groups, $C_1$–$C_4$ lower alkoxy groups such as benzyloxy, methoxy, ethoxy, and t-butoxy, $C_1$–$C_4$ lower alkoxycarbonyl groups such as methoxycarbonyl and ethoxycarbonyl, and aryl groups such as phenyl, p-methoxyphenyl, p-tolyl, and 2-naphthyl), and aryl groups such as phenyl, p-methoxyphenyl, p-tolyl, and 2-naphthyl.

Preferred examples of $R^2$ in the β-keto ester compound (I) include alkyl groups such as methyl, ethyl, propyl, butyl, pentyl, hexyl, and octyl and a benzyl group which may have one or more substituents. Preferred examples of the substituents include methyl, ethyl, and methoxy.

Specific examples of the β-keto ester compound (I) include methyl acetoacetate, ethyl acetoacetate, n-propyl acetoacetate, isopropyl acetoacetate, n-butyl acetoacetate, t-butyl acetoacetate, n-pentyl acetoacetate, n-hexyl acetoacetate, n-octyl acetoacetate, benzyl acetoacetate, methyl 4-chloroacetoacetate, ethyl 4-chloroacetoacetate, methyl 3-oxopentanoate, methyl 3-oxohexanoate, methyl 3-oxoheptanoate, methyl 6-methyl-3-oxoheptanoate, methyl 3-oxooctanoate, methyl 3-oxononanoate, methyl 3-oxodecanoate, methyl 3-oxoundecanoate, methyl 3-oxododecanoate, methyl 3-oxotridecanoate, methyl 3-oxotetradecanoate, methyl 3-oxopentadecanoate, methyl 3-oxohexadecanoate, methyl 3-oxoheptadecanoate, methyl 3-oxooctadecanoate, ethyl 3-oxopentanoate, ethyl 3-oxohexanoate, ethyl 3-oxoheptanoate, ethyl 3-oxooctanoate, ethyl 3-oxononanoate, ethyl 3-oxodecanoate, ethyl 3-oxoundecanoate, ethyl 3-oxododecanoate, ethyl 3-oxotridecanoate, ethyl 3-oxotetradecanoate, ethyl 3-oxopentadecanoate, ethyl 3-oxohexadecanoate, ethyl 3-oxoheptadecanoate, ethyl 3-oxooctadecanoate, methyl benzoylacetate, ethyl benzoylacetate, methyl 4-phenyl-3-oxobutanoate, methyl 4-benzyloxyacetoacetate, methyl 4-methoxyacetoacetate, dimethyl 3-oxooctanedioate, diethyl 3-oxooctanedioate, methyl 4-dimethylamino-3-oxobutanoate, ethyl 4-dimethylamino-3-oxobutanoate, methyl 4-amino-3-oxobutanoate hydrochloride, methyl 4-amino-3-oxobutanoate p-toluenesulfonate, methyl 4-amino-3-oxobutanoate methanesulfonate, 3-(ethoxycarbonyl)-2-oxopropyltrimethylammonium chloride, 3-(methoxycarbonyl)-2-oxopropyltrimethylammonium chloride, and methyl 4-benzyloxycarbonylamino-3-oxobutanoate.

The optically active tertiary diphosphine compound to be used in the invention is represented by the following general formula (II):

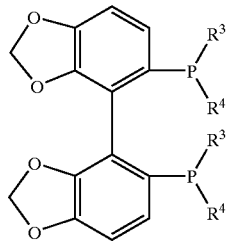

(II)

(wherein $R^3$ and $R^4$ each independently represent a cycloalkyl group, an unsubstituted or substituted phenyl group, or a five-membered heteroaromatic ring residue). Preferred examples of the cycloalkyl groups represented by $R^3$ and $R^4$ include cyclopentyl, cyclohexyl, and cycloheptyl. Preferred examples of the five-membered heteroaromatic ring residues represented by $R^3$ and $R^4$ include 2-furyl, 3-furyl, 2-benzofuryl, and 3-benzofuryl. Examples of the substituents of the substituted phenyl groups include $C_1$–$C_5$ lower alkyl groups, $C_1$–$C_5$ lower alkoxy groups, di(lower alkyl)amino groups, and halogen atoms. The term "lower alkyl" as used herein means alkyl groups having 1 to 5 carbon atoms.

Preferred of the compounds represented by general formula (II) are compounds represented by formula (X):

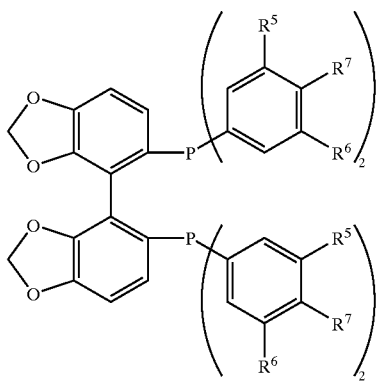

(X)

(wherein $R^5$ and $R^6$ each independently represent a hydrogen atom, a $C_1$–$C_4$ alkyl group, or a $C_1$–$C_4$ alkoxy group, and $R^7$ represents a hydrogen atom, a $C_1$–$C_4$ alkyl group, a $C_1$–$C_4$ alkoxy group, or a di($C_1$–$C_4$ alkyl)amino group).

More preferred are compounds represented by formula

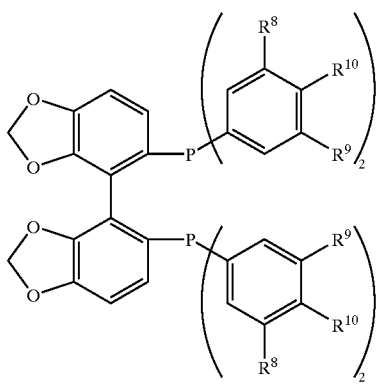

(XI)

(wherein $R^8$ and $R^9$ are the same and each represent a hydrogen atom, t-butyl, n-butyl, n-propyl, isopropyl, ethyl, or methyl, and $R^{10}$ represents a hydrogen atom, t-butoxy, isopropoxy, ethoxy, or methoxy).

The optically active tertiary diphosphine compound described above is known, and can be synthesized, for example, by the method described in JP-A-2000-16997 or JP-A-10-182678 corresponding to U.S. Pat. No. 5,872,273 (the term "JP-A" as used herein means an "unexamined published Japanese patent application").

The ruthenium complex to be used in the invention is a complex having the optically active tertiary diphosphine compound as a ligand, and is a known compound. Preferred examples of the complex are the following complexes represented by general formulae (IV) to (IX):

ruthenium-optically active tertiary phosphine complexes represented by:

[Ru₂X₄(L)₂](A)    (IV)

(wherein X represents a halogen atom, L represents an optically active tertiary phosphine ligand, and A represents a tertiary amine);

ruthenium-optically active tertiary diphosphine complexes represented by:

[RuX(arene)(L)]X    (V)

(wherein X and L are the same as defined above, and arene represents an optionally substituted benzene ring, preferred examples of which include benzene, toluene, xylene, cumene, p-cymene, ethylbenzene, and anisole);

ruthenium-optically active tertiary diphosphine complexes represented by:

[Ru(G)₂(L)]    (VI)

(wherein L is the same as defined above, and G represents a halogen atom or an acetoxy group);

ruthenium-optically active tertiary diphosphine complexes represented by:

[Ru(L)](J)₂    (VII)

(wherein L is the same as defined above, and J represents $BF_4$, $ClO_4$, $PF_6$, or $BPh_4$ (wherein Ph represents a phenyl group));

ruthenium-optically active tertiary diphosphine complexes represented by:

[{RuX(L)}₂(μ-X)₃][NH₂Q₂]    (VIII)

(wherein L and X are the same as defined above, and Q represents a hydrogen atom, a lower alkyl group having 1 to 6 carbon atoms, such as methyl, ethyl, propyl, isopropyl, butyl, isobutyl, t-butyl, or cyclohexyl, a phenyl group which may have one or more substituents, or a benzyl group which may have one or more substituents) (preferred examples of substituents of the phenyl group include methyl, ethyl, methoxy, and ethoxy, and examples of the benzyl group which may have one or more substituents include 1-phenethyl); and ruthenium-optically active tertiary diphosphine complexes represented by:

RuX₂(L)(DMF)ₙ    (IX)

(wherein X and L are the same as defined above, n is an integer of 1 to 3, and DMF represents N,N-dimethylformamide).

Preferred examples of the complexes described above include the following.

[Ru₂Cl₄(SEGPHOS)₂](NEt₃)
  ["SEGPHOS" means [4,4'-bis-1,3-benzodioxol]-5,5'-diylbis(diphenylphosphine)]
[Ru₂Cl₄(p-Tol-SEGPHOS)₂](NEt₃)
  ["p-Tol-SEGPHOS" means [4,4'-bis-1,3-benzodioxol]-5,5'-diylbis(di-p-tolylphosphine)]
[Ru₂Cl₄(DM-SEGPHOS)₂](NEt₃)
  ["DM-SEGPHOS" means [4,4'-bis-1,3-benzodioxol]-5,5'-diylbis(di-3,5-dimethylphenylphosphine)]
[RuCl(C₆H₆)(SEGPHOS)]Cl
[RuBr(C₆H₆)(SEGPHOS)]Br
[RuI(C₆H₆)(SEGPHOS)]I
[RuCl(p-cymene)(SEGPHOS)]Cl
[RuBr(p-cymene)(SEGPHOS)]Br
[RuI(p-cymene)(SEGPHOS)]I
[RuCl(C₆H₆)(p-Tol-SEGPHOS)]Cl
[RuBr(C₆H₆)(p-Tol-SEGPHOS)]Br
[RuI(C₆H₆)(p-Tol-SEGPHOS)]I
[RuCl(p-cymene)(p-Tol-SEGPHOS)]Cl
[RuBr(p-cymene)(p-Tol-SEGPHOS)]Br
[RuI(p-cymene)(p-Tol-SEGPHOS)]I
[RuCl(C₆H₆)(DM-SEGPHOS)]Cl
[RuBr(C₆H₆)(DM-SEGPHOS)]Br
[RuI(C₆H₆)(DM-SEGPHOS)]I

[RuCl(p-cymene)(DM-SEGPHOS)]Cl
[RuBr(p-cymene)(DM-SEGPHOS)]Br
[RuI(p-cymene)(DM-SEGPHOS)]I
[Ru(OAc)$_2$(SEGPHOS)]
["OAc" represents an acetoxy group]
[Ru(OAc)$_2$(p-Tol-SEGPHOS)]
[Ru(OAc)$_2$(DM-SEGPHOS)]
[RuBr$_2$(SEGPHOS)]
[RuBr$_2$(p-Tol-SEGPHOS)]
[RuBr$_2$(DM-SEGPHOS)]
[Ru(SEGPHOS)](BF$_4$)$_2$
[Ru(SEGPHOS)](ClO$_4$)$_2$
[Ru(SEGPHOS)](PF$_6$)$_2$
[Ru(p-Tol-SEGPHOS)](BF$_4$)$_2$
[Ru(p-Tol-SEGPHOS)](ClO$_4$)$_2$
[Ru(p-Tol-SEGPHOS)](PF$_6$)$_2$
[Ru(DM-SEGPHOS)](BF$_4$)$_2$
[Ru(DM-SEGPHOS)](ClO$_4$)$_2$
[Ru (DM-SEGPHOS)](PF$_6$)$_2$
[{RuCl(SEGPHOS)}$_2$($\mu$-Cl)$_3$][NH$_2$Me$_2$]
[{RuCl(SEGPHOS)}$_2$($\mu$-Cl)$_3$][NH$_2$Et$_2$]
[{RuCl(p-Tol-SEGPHOS)}$_2$($\mu$-Cl)$_3$][NH$_2$Me$_2$]
[{RuCl(p-Tol-SEGPHOS)}$_2$($\mu$-Cl)$_3$][NH$_2$Et$_2$]
[{RuCl(DM-SEGPHOS)}$_2$($\mu$-Cl)$_3$][NH$_2$Me$_2$]
[{(RuCl(DM-SEGPHOS)}$_2$($\mu$-Cl)$_3$][NH$_2$Et$_2$]
["Me" represents a methyl group and "Et" represents an ethyl group]
RUCl$_2$(SEGPHOS)(DMF)$_n$
RuCl$_2$(p-Tol-SEGPHOS)(DMF)$_n$
RuCl$_2$(DM-SEGPHOS)(DMF)$_n$
["DMF" represents N,N-dimethylformamide]

The complexes shown above can be prepared, for example, by the method described in JP-A-10-182678 or JP-A-11-269185.

The process of the invention for preparing an optically active alcohol will be explained below. The β-keto ester compound (I) described above, as a starting material, is asymmetrically hydrogenated in a solvent in the presence of the ruthenium complex, whereby an optically active alcohol can be prepared. Preferred examples of the solvent include protic solvents such as methanol, ethanol, and isopropyl alcohol. Also preferred is a mixed solvent composed of one or more such protic solvents and one or more of other solvents such as tetrahydrofuran, toluene, benzene, methyl acetate, ethyl acetate, methylene chloride, and the like. It is more preferred that the β-keto ester compound (I) be dissolved in the solvent before being subjected to asymmetric hydrogenation reaction.

In order for the asymmetric hydrogenation reaction to proceed satisfactorily, the ruthenium complex is added to the solvent in an amount of preferably from 1/100 to 1/100,000 mol, more preferably from 1/1,000 to 1/50,000 mol, per mol of the β-keto ester compound. This asymmetric hydrogenation reaction is generally conducted for from 1 to 48 hours with stirring under the conditions of a hydrogen pressure of from 0.1 to 10 MPa, preferably from 1 to 5 MPa, and a temperature of from 0 to 150° C., preferably from 20 to 100° C.

In the invention, the selectivity and conversion of the β-keto ester compound as a starting material can be improved by conducting the asymmetric hydrogenation reaction in the presence of an acid. Preferred examples of the acid include mineral acids such as sulfuric acid and organic acids such as methanesulfonic acid, p-toluenesulfonic acid, and benzenesulfonic acid. In this case, such an acid is added in an amount of generally from 0.5 to 10 mole equivalents, preferably from 0.7 to 8 mole equivalents, more preferably from 0.9 to 5 mole equivalents, to the ruthenium complex.

After completion of the asymmetric hydrogenation reaction, the hydrogenation product may be purified in an ordinary manner. Usable purification techniques include a method in which the solvent is removed by distillation and the resulting residue is distilled under reduced pressure, a method in which the hydrogenation product is purified by silica gel column chromatography, and a method in which the hydrogenation product is purified by recrystallization.

The optically active alcohol (III) obtained by the process of the invention will be explained below. The optically active alcohol (III) corresponds to the β-keto ester compound used as a starting material. This is because the keto group of the β-keto ester compound is reduced to a hydroxyl group to give the optically active alcohol (III). Furthermore, either of the (R) isomer and the (S) isomer of the optically active alcohol can be obtained according to the selection of the ruthenium complex.

More specifically, different ruthenium complexes behave in the manners shown by the following scheme 1.

(Scheme 1)

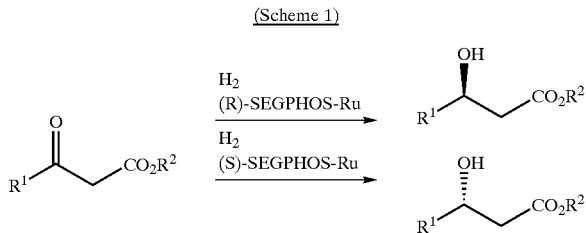

It has therefore become possible to freely prepare the optically active alcohol having the desired absolute configuration by selecting a ruthenium complex.

Examples of the optically active alcohol include methyl 3-hydroxybutanoate, ethyl 3-hydroxybutanoate, octyl 3-hydroxybutanoate, benzyl 3-hydroxybutanoate, ethyl 4-chloro-3-hydroxybutanoate, ethyl 6-methyl-3-hydroxyheptanoate, methyl 3-hydroxytetradecanoate, ethyl 4-phenyl-3-hydroxybutanoate, ethyl 3-phenyl-3-hydroxypropionate, and ethyl 4-N-benzyloxycarbonylamino-3-hydroxybutanoate, which all are optically active.

According to the invention, it has become possible to produce an optically active alcohol by the practical process. Namely, the invention has made it possible to efficiently produce through a simple operation an optically active alcohol having a high optical purity and a specific absolute configuration. Because of this, optically active alcohols useful as intermediates for medicines or as functional materials, etc. have become easily producible. Furthermore, by conducting the reaction in the presence of a specific acid, selectivity can be greatly improved while keeping the high optical purity almost unchanged.

The invention will be explained below in more detail by reference to Examples, but the invention should not be construed as being limited to these Examples in any way. The optically active tertiary diphosphine compound used in the invention was synthesized by the method described in JP-A-2000-16997 or JP-A-10-182678. The ruthenium-optically active tertiary diphosphine complexes used were prepared by the method described in JP-A-10-182678.

Among the β-keto ester compounds used in the invention, ethyl 4-benzyloxyacetoacetate was synthesized by the method described in JP-A-6-6522, while methyl benzoylacetate, dimethyl 3-oxooctanedioate, methyl 3-oxooctadecanoate, methyl 3-oxotetradecanoate, methyl 6-methyl-3-oxoheptanoate, and methyl 4-phenyl-3- oxobutanoate were synthesized by the methods described in Yuji Oikawa et al., *J. Org. Chem.*, Vol.43, pp.2087–2088 (1978) and Heinz Thoma et al., *Liebigs Ann. Chem.*, pp.1237–1248. Furthermore, methyl 4-amino-3-oxobutanoate hydrochloride was synthesized by the method described in JP-A-11-286479.

The following analytical instruments or means were used.
Determination of Asymmetric Yield
  High-performance liquid chromatograph HPLC:
    Waters 2690 (manufactured by Waters Inc.)
    Detector, Waters 996 (manufactured by Waters Inc.)
  Gas Chromatograph:
    HP5890 series (manufactured by Hewlett Packard Co.)
Determination of Selectivity
  Gas Chromatograph:
    HP5890 series (manufactured by Hewlett Packard Co.)

EXAMPLE 1

Asymmetric Hydrogenation of Methyl Benzoylacetate

Into a 1-L autoclave was introduced methanol (360 mL) in a nitrogen stream. Then, [{RuCl((R)-SEGPHOS)}$_2$($\mu$-Cl)$_3$][Me$_2$NH$_2$] (82 mg: 0.1 mmol) and methyl benzoylacetate (178 g: 1.0 mol) were added. After hydrogen (4.0 MPa) was forced into the autoclave, the reaction mixture was heated to 80° C. and stirred for 5.5 hours to carry out asymmetric hydrogenation reaction. After cooling, methanol was removed from the reaction mixture, and the residue was distilled under reduced pressure (94–99° C./133 Pa) to obtain 170.6 g (yield, 95.3%) of methyl (S)-3-hydroxy-3-phenylpropionate. The asymmetric yield thereof was determined with the HPLC (CHIRALCEL OD-H, 4.6 mm×250 mm; hexane/isopropyl alcohol=95/5; flow rate, 1.0 mL/min; detection wavelength, UV-254 nm), and was found to be 97.2%.

EXAMPLE 2

Asymmetric Hydrogenation of Methyl 3-Oxooctadecanoate

Into a 100-mL autoclave were introduced methyl 3-oxooctadecanoate (2.0 g: 6.4 mmol), methanol (6 mL), methylene chloride (3 mL), and [{RuCl((R)-SEGPHOS)}$_2$($\mu$-Cl)$_3$][Et$_2$NH$_2$] (5.2 mg: 0.0064 mmol). After hydrogen (3.0 MPa) was forced into the autoclave, the reaction mixture was heated to 50° C. and stirred for 15 hours to carry out asymmetric hydrogenation reaction and thereby obtain methyl (R)-3-hydroxyoctadecanoate.

The reaction mixture was cooled to room temperature and then analyzed with the HPLC (CHIRALCEL OD-H, 4.6 mm×250 mm; hexane/isopropyl alcohol=98/2; flow rate, 1.0 mL/min; detection wavelength, UV-210 nm) to determine the asymmetric yield of the optically active compound. As a result, the yield was found to be 99.5%.

EXAMPLE 3

Asymmetric Hydrogenation of Methyl 3-Oxotetradecanoate

Into a 100-mL autoclave were introduced methyl 3-oxotetradecanoate (2.0 g: 7.8 mmol), methanol (6 mL), and [{RuCl((R)-SEGPHOS)}$_2$($\mu$-Cl)$_3$][Et$_2$NH$_2$] (6.6 mg: 0.0078 mmol) After hydrogen (3.0 MPa) was forced into the autoclave, the reaction mixture was heated to 50° C. and stirred for 15 hours to conduct asymmetric hydrogenation reaction and thereby obtain methyl (R)-3-hydroxytetradecanoate.

The reaction mixture was cooled to room temperature and then analyzed with the HPLC (CHIRALCEL OD-H, 4.6 mm×250 mm; hexane/isopropyl alcohol=98/2; flow rate, 1.0 mL/min; detection wavelength, UV-210 nm) to determine the asymmetric yield of the optically active compound. As a result, the yield was found to be 97.0%.

EXAMPLE 4

Asymmetric Hydrogenation of Methyl 6-Methyl-3-oxoheptanoate

Into a 100-mL autoclave were introduced methyl 6-methyl-3-oxoheptanoate (2.0 g: 11.6 mmol), methanol (2 mL), and [{RuCl((R)-SEGPHOS)}$_2$($\mu$-Cl)$_3$][Me$_2$NH$_2$] (9.5 mg: 0.0116 mmol). After hydrogen (5.0 MPa) was forced into the autoclave, the reaction mixture was heated to 50° C. and stirred for 15 hours to conduct asymmetric hydrogenation reaction and thereby obtain methyl (R)-6-methyl-3-hydroxyheptanoate.

The reaction mixture was cooled to room temperature and then analyzed with the HPLC (CHIRALCEL OB, 4.6 mm×250 mm; hexane/isopropyl alcohol=1999/1; flow rate, 0.7 mL/min; detection wavelength, UV-210 nm) to determine the asymmetric yield of the optically active compound. As a result, the yield was found to be 98.5%.

EXAMPLE 5

Asymmetric Hydrogenation of Methyl 4-Phenyl-3-oxobutanoate

Into a 100-mL autoclave were introduced methyl 4-phenyl-3-oxobutanoate (2.0 g: 10.4 mmol), methanol (2 mL), and [{RuCl((R)-SEGPHOS)}$_2$($\mu$-Cl)$_3$][Me$_2$NH$_2$] (8.5 mg: 0.0104 mmol). After hydrogen (5.0 MPa) was forced into the autoclave, the reaction mixture was heated to 50° C. and stirred for 15 hours to conduct asymmetric hydrogenation reaction and thereby obtain methyl (S)-4-phenyl-3-hydroxybutanoate.

The reaction mixture was cooled to room temperature and then analyzed with the HPLC (CHIRALCEL OB, 4.6 mm×250 mm; hexane/isopropyl alcohol=1999/1; flow rate, 0.7 mL/min; detection wavelength, UV-210 nm) to determine the asymmetric yield of the optically active compound. As a result, the yield was found to be 97.9%.

EXAMPLE 6

Asymmetric Hydrogenation of Ethyl 4-Chloroacetoacetate

Into a 500-mL autoclave was introduced [{RuCl((R)-SEGPHOS)}$_2$($\mu$-Cl)$_3$][Me$_2$NH$_2$] (122 mg: 0.149 mmol). After the atmosphere in the autoclave was replaced with nitrogen, distilled ethanol (183 mL) and ethyl 4-chloroacetoacetate (60.9 g: 0.37 mol) were added thereto. The autoclave was heated until the temperature of the contents reached 90° C. and hydrogen (3.0 MPa) was forced into the autoclave to react the reaction mixture for 2 hours, during which the hydrogen pressure of 3.0 MPa was maintained. After completion of the reaction, the solvent was removed and the residue was distilled under reduced pressure to obtain ethyl (S)-4-chloro-3-hydroxybutanoate (54.6 g: yield, 88.5%).

The asymmetric yield thereof was determined by gas chromatography (Chiraldex G-TA, 0.25 mmI.D.×30 m×0.125 $\mu$m; initial temp., 80° C.; final temp., 110° C.; rate, 1.0 ° C./min; injection temp., 200° C.; detector temp., 200° C.), and was found to be 98.5%.

EXAMPLE 7

Asymmetric Hydrogenation of Ethyl 4-Benzyloxyacetoacetate

Into a 100-mL autoclave were introduced ethyl 4-benzyloxyacetoacetate (3.0 g: 12.7 mmol), ethanol (3 mL), [{RuCl((R)-SEGPHOS)}$_2$($\mu$-Cl)$_3$][Me$_2$NH$_2$] (1.5 mg: 0.0018 mmol), and water (0.03 mL). After the contents were heated to 95° C., hydrogen (3 MPa) was forced into the autoclave. The reaction mixture was stirred for 1 hour to conduct asymmetric hydrogenation reaction and thereby obtain methyl (S)-4-benzyloxy-3-hydroxybutanoate.

The reaction mixture was cooled to room temperature and then analyzed with the HPLC (Chiralpak AD-RH, 4.6 mm×250 mm; acetonitrile/water=35/65; flow rate, 0.5 mL/min; detection wavelength, UV-220 nm) to determine the asymmetric yield of the optically active compound. As a result, the yield was found to be 99.4%.

EXAMPLE 8

Asymmetric Hydrogenation of Methyl 4-Amino-3-oxobutanoate Hydrochloride

Into a 100 mL autoclave were introduced methyl 4-amino-3-oxobutanoate hydrochloride (1.7 g: 11 mmol), methanol (5.1 mL), and [{RuCl((R)-SEGPHOS)}$_2$($\mu$-Cl)$_3$][Me$_2$NH$_2$] (9.1 mg: 0.011 mmol). Hydrogen (3 MPa) was forced into the autoclave, and the reaction mixture was heated to 50° C. and stirred for 17 hours to carry out asymmetric hydrogenation reaction and thereby obtain methyl (S)-4-amino-3-hydroxyoctadecanoate hydrochloride.

The following operation was carried out in order to determine the asymmetric yield of the product of asymmetric hydrogenation. The reaction mixture was cooled to room temperature. Thereto were added methanol (3.5 mL) and 28% sodium methylate methanol solution (1.8 g). This mixture was reacted at 40° C. for 5 hours to convert the product of asymmetric hydrogenation into 4-hydroxy-2-pyrrolidone. The resultant reaction mixture was analyzed with the HPLC (Chiralpak AD, 4.6 mm×250 mm; hexane/ethanol/methanol=95/5/3; flow rate 0.8 mL/min; detection wavelength, UV-215 nm). As a result, the asymmetric yield of the optically active compound was found to be 91.8%.

EXAMPLE 9

Asymmetric Hydrogenation of Dimethyl 3-Oxooctanedioate

Into a 100-mL autoclave were introduced dimethyl 3-oxooctanedioate (2.2 g: 10.2 mmol), methanol (6.6 mL), and [Ru$_2$Cl$_4$((R)-SEGPHOS)$_2$](NEt$_3$) (3.7 mg: 0.003 mmol). Hydrogen (3.0 MPa) was forced into the autoclave, and the reaction mixture was heated to 70° C. and stirred for 7 hours to carry out asymmetric hydrogenation reaction and thereby obtain dimethyl (R)-3-hydroxyoctanedioate.

The reaction mixture was cooled to room temperature and then analyzed with the HPLC (CHIRALCEL OD-H, 4.6 mm×250 mm; hexane/isopropyl alcohol=90/10; flow rate, 0.5 mL/min; detection wavelength, UV-220 nm) to determine the asymmetric yield of the optically active compound. As a result, the yield was found to be 98.5%. Furthermore, the selectivity to the optically active compound was determined with the gas chromatograph (Neutrabond-1, 0.25 mmI.D.×30 m×0.125 $\mu$m; initial temp., 100° C.; final temp., 250° C.; rate, 5.0° C./min; injection temp., 220° C.; detector temp., 250° C.), and was found to be 68%.

EXAMPLE 10

Asymmetric Hydrogenation of Dimethyl 3-Oxooctanedioate

Into a 100-mL autoclave were introduced dimethyl 3-oxooctanedioate (2.2 g: 10.2 mmol), methanol (6.6 mL), [Ru$_2$Cl$_4$((R)-SEGPHOS)$_2$](NEt$_3$) (3.4 mg: 0.002 mmol), and p-toluenesulfonic acid monohydrate (3.8 mg: 0.02 mmol). Hydrogen (3.0 MPa) was forced into the autoclave, and the reaction mixture was heated to 80° C. and stirred for 6 hours to carry out asymmetric hydrogenation reaction and thereby obtain dimethyl (R)-3-hydroxyoctanedioate ester.

The reaction mixture was cooled to room temperature and then analyzed with the HPLC (CHIRALCEL OD-H, 4.6 mm×250 mm; hexane/isopropyl alcohol=90/10; flow rate, 0.5 mL/min; detection wavelength, UV-220 nm) to determine the asymmetric yield of, the optically active compound. As a result, the yield was found to be 99.2%. Furthermore, the selectivity to the optically active compound was determined with the gas chromatograph (Neutrabond-1, 0.25 mm I.D.×30 m×0.125 $\mu$m; initial temp., 100° C.; final temp., 250° C.; rate, 5.0° C./min; injection temp., 220° C.; detector temp., 250° C.), and was found to be 99%.

While the invention has been described in detail and with reference to specific embodiments thereof, it will be apparent to one skilled in the art that various changes and modifications can be made therein without departing from the spirit and scope thereof.

This application is based on Japanese patent application No. 2000-223521 filed on Jul. 25, 2000, the entire contents thereof being hereby incorporated by reference.

What is claimed is:

1. A process for producing an optically active alcohol represented by the following general formula (III):

(III)

(wherein R$^1$ represents a C$_1$–C$_{15}$ alkyl group which may have one or more substituents (selected from halogen atoms, a hydroxyl group, an amino group, amino groups protected by a protective group, amino groups protected by a mineral acid or organic acid, amino groups substituted with one or more C$_1$–C$_4$ lower alkyl groups, a benzyloxy group, C$_1$–C$_4$ lower alkoxy groups, C$_1$–C$_4$ lower alkoxycarbonyl groups, and aryl groups) or an aryl group; and R$^2$ represents a C$_1$–C$_8$ lower alkyl group, or a benzyl group which may have one or more substituents)

which comprises asymmetrically hydrogenating a $\beta$-keto ester compound represented by the following general formula (I):

(I)

(wherein R$^1$ and R$^2$ are the same as defined above) in the presence of at least one ruthenium complex comprising as a ligand an optically active tertiary diphosphine compound represented by the following general formula (II):

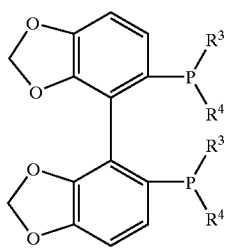

(II)

(wherein R³ and R⁴ each independently represent a cycloalkyl group, an unsubstituted or substituted phenyl group, or a five-membered heteroaromatic ring residue).

2. The process for producing an optically active alcohol of claim 1, wherein the ruthenium complex comprising an optically active tertiary diphosphine compound as a ligand is at least one complex selected from the following ruthenium complexes represented by general formulae (IV) to (IX):

ruthenium complexes represented by:

[Ru₂X₄(L)₂](A)  (IV)

(wherein X represents a halogen atom, L represents an optically active tertiary phosphine ligand, and A represents a tertiary amine);

ruthenium complexes represented by:

[RuX(arene)(L)]X  (V)

(wherein X and L are the same as defined above, and arene represents a benzene ring which may have one or more substituents);

ruthenium complexes represented by:

[Ru(G)₂(L)]  (VI)

(wherein L is the same as defined above, and G represents a halogen atom or an acetoxy group);

ruthenium complexes represented by:

[Ru(L)](J)₂  (VII)

(wherein L is the same as defined above, and J represents BF₄, ClO₄, PF₆, or BPh₄ (wherein Ph represents a phenyl group));

ruthenium complexes represented by:

[{RuX(L)}₂(μ-X)₃][NH₂Q₂]  (VIII)

(wherein L and X are the same as defined above, and Q represents a hydrogen atom, a lower alkyl group, a phenyl group which may have one or more substituents, or a benzyl group which may have one or more substituents); and ruthenium complexes represented by:

RuX₂(L)(DMF)ₙ  (IX)

(wherein X and L are the same as defined above, n is an integer of 1 to 3, and DMF represents N,N-dimethylformamide).

3. The process for producing an optically active alcohol of claim 1, wherein the asymmetric hydrogenation is carried out in the presence of an acid besides the ruthenium complex.

* * * * *